(12) United States Patent
Mehring (10) Patent No.: US 12,135,832 B2
(45) Date of Patent: Nov. 5, 2024

(54) INPUT APPARATUS FOR OPERATING OR CONTROLLING A TECHNICAL DEVICE

(71) Applicant: Universität Stuttgart, Stuttgart (DE)

(72) Inventor: Carsten Mehring, Stuttgart (DE)

(73) Assignee: Universität Stuttgart, Stuttgart (DE)

( * ) Notice: Subject to any disclaimer, the term of this patent is extended or adjusted under 35 U.S.C. 154(b) by 0 days.

(21) Appl. No.: 18/073,078

(22) Filed: Dec. 1, 2022

(65) Prior Publication Data
US 2023/0102363 A1  Mar. 30, 2023

Related U.S. Application Data

(63) Continuation of application No. PCT/EP2021/064258, filed on May 27, 2021.

(30) Foreign Application Priority Data

Jun. 2, 2020 (DE) .................. 102020114632.9

(51) Int. Cl.
*G06F 3/01* (2006.01)
*G06K 19/077* (2006.01)

(52) U.S. Cl.
CPC .............. *G06F 3/011* (2013.01); *G06F 3/016* (2013.01); *G06K 19/07758* (2013.01)

(58) Field of Classification Search
None
See application file for complete search history.

(56) References Cited

U.S. PATENT DOCUMENTS

| 7,995,031 | B2 | 8/2011 | Manal |
| 8,018,320 | B2 | 9/2011 | Najanguaq Søvsø Andreasen Struijk |
| 8,242,880 | B2 | 8/2012 | Ghovanloo et al. |
| 8,487,769 | B2 | 7/2013 | Lindsay et al. |

(Continued)

FOREIGN PATENT DOCUMENTS

| EP | 0487027 | 5/1992 |
| WO | WO90/07249 | 6/1990 |
| WO | WO2006/073296 | 7/2006 |

OTHER PUBLICATIONS

English Translation of International Preliminary Examination Report for PCT/EP2021/064258, mailed Dec. 8, 2022.

(Continued)

*Primary Examiner* — Amare Mengistu
*Assistant Examiner* — Sarvesh J Nadkarni
(74) *Attorney, Agent, or Firm* — Klarquist Sparkman, LLP (57) ABSTRACT

An input apparatus for operating and/or controlling a technical device includes a plurality of sensor elements which can be arranged spatially distributed in the oral cavity of a user. An interface circuit is coupled to the sensor elements and is configured to detect a respective current tongue position and/or tongue movement by means of the sensor elements. The interface circuit generates one or more control signals depending on the respective current tongue position and/or tongue movement and transmits the one or more control signals to the technical device. Advantageously, the sensor elements each include a transponder which is configured to receive an interrogation signal from the interface circuit and, in response thereto, to transmit an individually coded response signal to the interface circuit.

16 Claims, 2 Drawing Sheets

(56) References Cited

U.S. PATENT DOCUMENTS

| | | | |
|---|---|---|---|
| 8,548,394 B2 | 10/2013 | Christensen | |
| 2012/0259554 A1* | 10/2012 | Chen | A61F 4/00 |
| | | | 702/19 |
| 2013/0090921 A1 | 4/2013 | Liu et al. | |
| 2016/0154468 A1 | 6/2016 | Kimmel | |
| 2018/0000563 A1* | 1/2018 | Shanjani | A61B 5/682 |
| 2019/0192259 A1* | 6/2019 | Kopelman | A61B 5/682 |
| 2020/0113654 A1* | 4/2020 | Akselrod | A61B 5/0534 |

OTHER PUBLICATIONS

International Preliminary Examination Report for PCT/EP2021/064258, mailed Jun. 8, 2022.

International Search Report for PCT/EP2021/064258, mailed Sep. 8, 2021.

\* cited by examiner

INPUT APPARATUS FOR OPERATING OR CONTROLLING A TECHNICAL DEVICE

CROSS REFERENCES TO RELATED APPLICATIONS

This application is a continuation of international patent application PCT/EP2021/064258 filed on May 27, 2021 designating the U.S., which international patent application claims priority from German patent application 10 2020 114 632.9 filed on Jun. 2, 2020. The entire contents of these priority applications are incorporated herein by reference.

BACKGROUND

The present invention relates to an input apparatus and a method for operating and/or controlling a technical device by a user.

There are various concepts for enabling a user to interact with a technical device and, in particular, to generate data and/or control commands for the technical device. Keyboard, computer mouse, so-called trackballs and touch-sensitive surfaces in the form of touchscreens or touchpads are known for entering data or commands into a computer. What these input apparatuses have in common is that the user typically needs his hands or at least one or more fingers to operate the technical device. Accordingly, this can be referred to as a manual input apparatus.

In addition, voice-controlled input apparatuses are increasingly being used. However, there are situations and constellations in which a user cannot interact with a technical device either manually or voice-controlled, for example, due to a physical disability or due to another manual activity being performed at the same time in an environment in which voice input could be unreliable, disruptive or even treacherous.

US 2012/0259554 A1 proposes an input apparatus for a computer in which a user's tongue movement is tracked within the oral cavity. In a first exemplary embodiment, the input apparatus includes a magnetic ball that is free to rotate within a ball cage. The ball cage containing the ball can be placed in the user's oral cavity via a mouthpiece, and the user can move the ball with his or her tongue. A magnetic sensor is provided outside the oral cavity to detect changes in the magnetic field of the ball. In a second exemplary embodiment, the input apparatus includes a plurality of pressure sensors or a plurality of capacitive sensors arranged on a mouthpiece that can be slid over the user's teeth. It is proposed here that the sensors be visibly placed on the outer or front surface of the teeth. The pressure sensors can detect sufficient pressure that a user can generate with his or her tongue. Capacitive sensors can detect the proximity of the tongue even without touching it. The signals from the sensors are to be transmitted wirelessly to a processor, which in this respect can serve as an interface circuit to a computer. Here, the required wireless signals are to be generated by the sensor elements in response to a specific tongue movement of the user. This suggests that the sensors require a power supply not shown in the details. In a third exemplary embodiment, US 2012/0259554 A1 proposes that the users tongue movement is tracked using a thermal camera located in the oral cavity. Other exemplary embodiments include microphones outside the oral cavity to track tongue movement. Overall, US 2012/0259554 A1 thus proposes a variety of concepts for enabling a user to operate and/or control a technical device with the tongue.

Another input apparatus for operating and/or controlling a technical device by means of the tongue is disclosed in US 2016/0154468 A1. In a first exemplary embodiment, the device includes a rod with integrated sensor elements, which is attached to the users tongue, for example by a piercing. The sensor elements in the rod may include a rotation rate sensor, a pressure sensor, and/or a touch-sensitive sensor, such that the user can interact with a technical device by placing the tongue against the palate or by other tongue movements. In another exemplary embodiment, a touch-sensitive sensor element may be arranged as a dental implant in the users oral cavity.

Yet another input apparatus for operating and/or controlling a technical device by means of the tongue is disclosed in U.S. Pat. No. 7,995,031 B2. In this case, the input apparatus includes pressure sensors that are placed under the palate. Another input apparatus with pressure sensors is disclosed in U.S. Pat. No. 8,242,880 B2. U.S. Pat. No. 8,018,320 B2 proposes a tongue-controlled input apparatus based on induction. U.S. Pat. No. 8,548,394 B2 discloses a tongue-controlled input apparatus that is placed under the palate and is based on induction, on a mechanical interaction or on a touch-sensitive surface.

From US 2018/0000563 A1 a radio module is known, which is used to monitor a tooth adjustment in the context of an orthodontic treatment. Furthermore, the radio module can be used to monitor parameters relating to a person's breathing and sleep. The radio module can be attached to a patient's teeth using a carrier.

WO 2006/073296 A1 discloses an RFID tag for attachment to a human tooth. The RFID tag includes a memory for storing personal information intended to identify the wearer, particularly in the event of an accident.

U.S. Pat. No. 8,487,769 B2 discloses a switchable RFID transponder. US 2013/090921 A1 discloses an input apparatus for voice input.

SUMMARY

Against this background, it is an object to provide an alternative input apparatus or method that enables reliable operation and/or control of a technical device by means of the tongue.

It is another object to provide an input apparatus or method that allows a large variety of user inputs and reduces incorrect inputs as much as possible.

It is another object to provide an input apparatus or method that allows a comfortable and harmless/unhazardous interaction with a technical device for the user by means of the tongue.

According to a first aspect, there is provided an input apparatus for at least one of operating or controlling a technical device, the apparatus comprising a plurality of sensor elements configured to be arranged spatially distributed in an oral cavity of a user in order to detect at least one of a respective current tongue position or respective tongue movement of the user, and comprising an interface circuit coupled to the sensor elements, wherein the interface circuit is configured to generate an interrogation signal, wherein the sensor elements each include a transponder configured to receive the interrogation signal and to transmit an individually encoded response signal in response to the interrogation signal, with each transponder being configured to generate the individually encoded response signal having an individual code identifying the respective transponder, and wherein the interface circuit is further configured to receive at least one individually encoded response signal from at least one sensor element and to generate a control signal for the at least one of operating or controlling the technical device as a function of the individually encoded response signal.

According to another aspect, there is provided a method for at least one of operating or controlling a technical device by a user, comprising the steps:

providing a plurality of sensor elements spatially distributed in an oral cavity of the user, detecting at least one of a respective current tongue position or respective tongue movement of the user using the sensor elements, generating a plurality of control signals depending on the at least one of the respective current tongue position or the respective tongue movement of the user by means of an interface circuit coupled to the sensor elements, and transmitting the plurality of control signals from the interface circuit to the technical device, wherein the interface circuit generates an interrogation signal, and wherein the sensor elements each include a transponder configured to receive the interrogation signal and to transmit an individually encoded response signal to the interface circuit as a function of the at least one of the respective current tongue position or respective tongue movement of the user.

In preferred exemplary embodiments of the method and apparatus, the sensor elements each include a passive transponder, i.e., a transponder that generates the transmission energy required to generate the individually encoded response signal from the interrogation signal or receives it with the interrogation signal. Accordingly, the sensor elements in the preferred exemplary embodiments do not require their own energy storage. In particular, a battery or rechargeable battery in the oral cavity can be dispensed with, which is of great advantage for avoiding health impairments.

Notwithstanding, however, the input apparatus could have an energy storage in the form of a battery, a rechargeable battery or a capacitor, for example in the form of a so-called supercap. The energy storage may be arranged in the oral cavity of the user together with the sensor elements. Preferably, such an energy storage may be charged without contact, in particular inductively or capacitively. In principle, such an energy store may also be charged by means of what is called "energy harvesting", such as by exploiting the kinetic energy of the tongue movement itself.

In any case, the sensor elements of the new input apparatus each have a transponder capable of transmitting an individually encoded response signal to the interface circuit. Thus, each sensor element has "its own" transponder that identifies the sensor element. As a result, the interface circuit can easily and reliably identify from which sensor element among the plurality of sensor elements a respective response signal originates. This makes it possible to detect the respective current position and/or movement of the tongue with a high spatial resolution and a high reliability.

In particular, the new input apparatus makes it possible in a very simple and cost effective way to provide a high number of teeth with one or even more sensor elements each, in order to realize in this way a high number of "keys" for convenient and accurate tongue-controlled input of data and/or control commands. The human tongue can locate teeth in the user's oral cavity with high specificity and spatial resolution. In addition, the human tongue can detect even the smallest elevations, depressions and changes in the oral cavity. The new input apparatus makes advantageous use of this property. In principle, one or more sensor elements could be arranged on each of the user's teeth, for example on different sides of a tooth including the inner side of the tooth facing the tongue, the outer side of the tooth facing away from the tongue, and possibly the occlusal surfaces. The new input apparatus thus opens up a large number of data and/or command inputs which can be very reliably distinguished from one another due to the individual coding of the transponders in each case, without the need for a complex evaluation circuit in the users oral cavity. In principle, it is possible with the new input apparatus to implement the assignment of a conventional computer keyboard with a corresponding ASCII character set.

A movement of the tongue along the inner sides of the teeth enables a user to interact very comfortably and without fatigue. Overall, a comfortable, reliable and safe interaction of a user with a technical device can therefore be realized with the new input apparatus.

In a preferred refinement, the sensor elements each are arranged on a sensor carrier that is configured to place the sensor elements on the user's teeth, in particular on the inner sides of the teeth facing the tongue.

In contrast or in addition to this, the sensor elements could be placed at other locations within the oral cavity of a user in other exemplary embodiments, for example on the palate or on the jaw bones. Placing the sensor elements on the teeth advantageously helps to enable error-free and comfortable interaction with the technical device, because the teeth represent a reference position that is known and familiar to the user. It is particularly advantageous to place the individual sensor elements on inner sides of the teeth, respectively, because the user can then reach the sensor elements with very little movements. In some exemplary embodiments, the sensor carrier may hold a single sensor element on a tooth at a time. In other exemplary embodiments, the sensor carrier may hold multiple sensor elements, for example, in the manner of a bridge and/or as a molded model adapted as a negative replica to the outer contour of one or more teeth. In some exemplary embodiments, the sensor carrier may include a silicone body that may be slid over the user's teeth in the manner of a dental guard or splint. In other exemplary embodiments, the sensor elements may be bonded to tooth surfaces, such that in these cases a housing wall of the respective sensor element, which may be fixed to one or more of the user's teeth using a body-compatible adhesive, forms or includes the sensor carrier. The positioning of these sensor elements can advantageously be carried out by means of an applicator. Multiple sensor elements may be arranged in groups on a common holder. In some exemplary embodiments, the input apparatus may include sensor carriers that can each hold two sensor elements per tooth.

In another refinement, the input apparatus comprises a holder configured to hold the interface circuit outside of the users oral cavity.

Preferably, the holder is configured to hold the interface circuit in the head and/or neck region of the user. In some exemplary embodiments, the holder may comprise a bracket that is arranged in the cheek area of the user in the intended use and may be attached to the head and/or ear of the user in the manner of a microphone headset, for example. In further exemplary embodiments, the holder may be arranged in front of the user's face in the manner of an eyeglass frame or may be placed around the user's neck on a collar or necklace. In further exemplary embodiments, the interface circuit may be implemented on a flexible film adhering to the skin or as a so-called electronic tattoo positioned in the cheek, chin and/or neck area of the user. All these exemplary embodiments and examples have the advantage that the individual coding can be transmitted and the interrogation signal and response signal can be exchanged over short distances. This allows the new input apparatus to be implemented with very low transmission power, which appears to be advantageous both for the operating time and for the health of the user.

In another refinement, the sensor elements each include a SAW tag as a transponder.

The abbreviation SAW stands for Surface Acoustic Wave and describes a sound wave that propagates on the surface of a body. In this refinement, the sensor elements include a wave transducer (typically an interdigital transducer) that converts an electrical, magnetic and/or electromagnetic interrogation signal into a mechanical sound wave. The sound wave can propagate along the surface of the carrier body and is reflected at defined reflection points. A sound wave reflected in this manner travels back along the surface of the body and is radiated by the wave transducer as a response signal. In preferred exemplary embodiments, each sensor element has a SAW tag with an individual coding in the form of a spatial distribution of reflection points, so that the individually coded response signal contains in each case a plurality of reflections whose temporal spacing relative to the interrogation signal and relative to each other represents the individual coding.

The use of such SAW tags enables very cost-effective and reliable identification of the individual sensor elements. The sound wave on the surface of the sensor element propagates more slowly than an electromagnetic radio wave, which in principle leads to a time delay between the interrogation signal and the individually coded response signals of the sensor elements. This time delay is very advantageous for evaluating a plurality of individually encoded response signals in response to a common interrogation signal, especially in the presence of natural reflections of the interrogation signal in the user's oral cavity. The delay also reduces direct crosstalk from the interrogation signal to the response signal at the interface circuit. In addition, unlike many other sensing elements, SAW tags can be manufactured with very small dimensions of, for example, less than or equal to 2 mm×2 mm×0.2 mm. This favors positioning directly on the user's teeth. In some exemplary embodiments, the SAW tags may be provided with a body-compatible coating and attached to the user's teeth using a body-compatible adhesive, Advantageously, such sensor elements can then be removed by simply brushing the teeth and excreted, for example, through the intestinal tract. This reduces or avoids hygiene problems.

In a further refinement, the interface circuit is configured to analyze a plurality of individually encoded response signals with respect to a respective signal strength.

In this refinement, the analysis of the sensor elements includes an analysis of the respective signal strength in addition to the interface circuit analyzing the respective individual encoding of the sensor elements. In some exemplary embodiments, the analysis of the respective signal strength may be performed using a threshold criterion in that the interface circuit first decides, based on a threshold criterion, which response signals from the plurality of response signals of the sensor elements are to be subjected to further analysis/evaluation. In some preferred exemplary embodiments, the interface circuit is configured to analyze only those individually coded response signals with respect to the respective individual code whose signal strength exceeds or at least reaches a defined threshold value. The refinement enables the new input apparatus to be implemented in a very simple and cost-effective manner with purely passive sensor elements, since the tongue attenuates or even suppresses a signal exchange between a sensor element and the interface circuit when it covers the sensor element. Accordingly, the input apparatus of this refinement may rely on the user to selectively attenuate and/or suppress a signal exchange between the interface circuit and one or more selected sensor elements using the user's tongue. Advantageously, the interface circuit may store which individually encoded response signals the interface circuit can expect in response to an interrogation signal when none of the sensor elements or only certain sensor elements are covered by the user with his tongue. The interface circuit may be configured to compare the received response signals to the expectation, thereby identifying from which sensor element or elements a response signal of sufficient signal strength has not been received. In this way, the interface circuit can very easily detect the "actuation" of a sensor element with the tongue, more precisely an intentional association between tongue and tooth or teeth.

In a further refinement, the interface circuit is arranged to logically interlink a plurality of individually encoded response signals.

This refinement advantageously contributes to the interface circuit being able to reliably detect and evaluate simultaneous and/or successive "actuations" of a group of sensor elements. Particularly advantageously, in some exemplary embodiments of this refinement, the interface circuit is configured to detect tongue movement along a plurality of sensor elements with respect to the direction of movement and/or speed of movement. This allows the user to interact with the technical device, for example, via "swipe" motions similar to a touch-sensitive screen of a smartphone or tablet PC. For example, a movement with the tongue from left to right along the inside of the teeth in the user's upper jaw could act as an input command to a technical device that triggers a movement of the device to the right. The technical device may be, for example, an assistive robotic system. This refinement also facilitates the detection and ignoring of possibly unintentional multiple actuations and a consequent increase in the reliability of the new input apparatus.

In a further refinement, the sensor elements each include a switch configured to selectively activate or deactivate the transponder.

In some exemplary embodiments of this refinement, the switch may be configured to selectively make or break an electrical connection between a first portion of the sensing element and a second portion of the sensing element, wherein the first portion of the sensing element includes an antenna through which the interrogation signal is received and/or the response signal is sent, while the second portion stores or represents the individual coding of the respective sensing element. In some exemplary embodiments, the switch may be an electrical contact that may be selectively closed by the tongue. In particular, the switch can include a changeover contact that can selectively activate a first sensor element or a second sensor element.

This refinement is particularly advantageous if the interface circuit is to receive an individually coded response signal only from those sensor elements that are selected by a user action. The refinement enables fast detection of a sensor element activated by the user with the tongue. It also helps to provide haptic feedback to the user for the actuation of a sensor element. This can be beneficial to reduce erroneous inputs.

In another refinement, the sensor elements each have a defined contact su face for the users tongue, and the switch can be actuated perpendicular to the contact surface.

In this refinement, the sensor elements can act in the manner of a pushbutton, which enables very reliable individual actuation of individual sensor elements with the tongue.

In another refinement, the sensor elements each have a defined contact area for the user's tongue, and the switch can be actuated parallel to the contact area.

In this refinement, activation of a sensor element requires, in a sense, a sliding actuation of the switch with the tongue or a shear force applied with the tongue, which advantageously helps to reduce erroneous inputs. Furthermore, this refinement is advantageous if a sensor element is to optionally generate two different response signals to further increase the number of possible interactions of the user with the technical device.

In a further refinement, the sensor elements each have an protrusion and/or indentation that provides a tactile marker for the user's tongue.

This refinement advantageously helps to improve the ergonomics of the new input apparatus and to minimize unintentional erroneous inputs.

In a further refinement, the input apparatus includes a jaw position sensor configured to detect a jaw position of the user, wherein the interface circuit is configured to generate the plurality of control signals further depending on the jaw position sensor.

This refinement advantageously helps to further increase the number of possible user inputs. In some preferred exemplary embodiments, the jaw position sensor can function in the manner of a shift key, such that the user can effect various interactions with the technical device by opening or closing his or her jaw in addition to moving the tongue. Accordingly, in preferred exemplary embodiments, the interface circuit is configured to generate various control signals to an individually encoded response signal from a selected sensor element in response to a signal from the jaw position sensor. In some exemplary embodiments, the jaw position sensor may be configured to detect an opening angle between the upper jaw and the lower jaw of the user. In further exemplary embodiments, the jaw position sensor may be configured to generate a pressure-dependent jaw position signal that may be representative of, for example, the pressure with which the upper jaw and the lower jaw are pressed against each other.

In a further refinement, the sensor elements each have a closed biocompatible shell.

In terms of this refinement, a biocompatible shell is a closed shell made of a material that is free of harmful influences when in contact with the user's saliva and/or tissue. In some exemplary embodiments, the sensor elements may be coated with proteins to achieve biocompatibility. The sensor elements of this refinement have high body compatibility and are preferably biotolerant or even bioinert.

It is understood that the above features and those yet to be explained below can be used not only in the combination indicated in each case, but also in other combinations or on their own, without departing from the scope of the present invention.

BRIEF DESCRIPTION OF THE DRAWING

Exemplary embodiments of the invention are shown in the drawing and are explained in more detail in the following description. In the drawing

EMBODIMENTS

Figure 1:
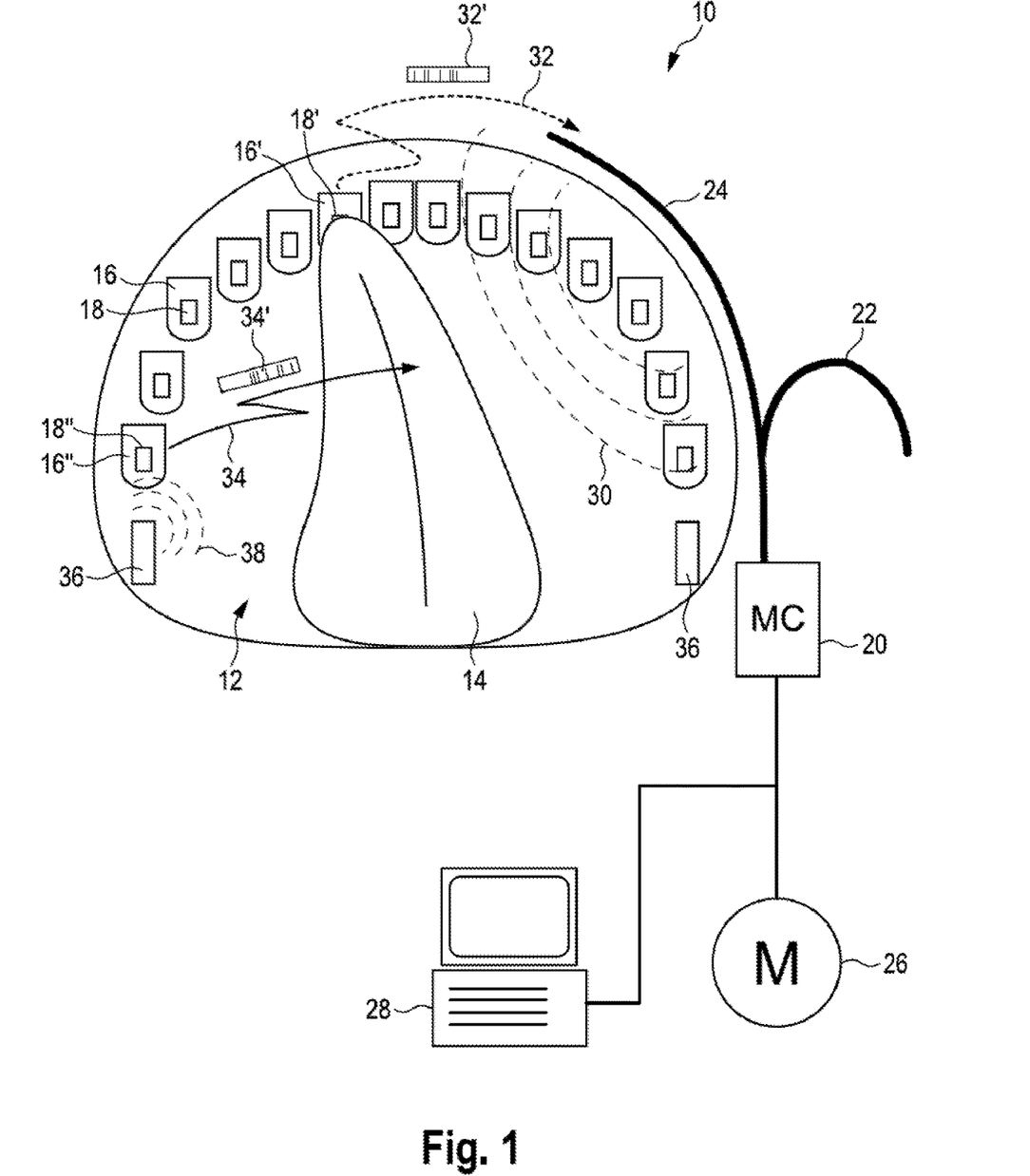
FIG. 1 shows schematic representation of a first exemplary embodiment of the new apparatus.

In FIG. 1, an exemplary embodiment of the new input apparatus is designated in its entirety by reference numeral 10. The input apparatus 10 is intended to enable a human user to interact with a technical device, as explained in detail below. The user is shown here in a highly simplified manner with his oral cavity 12, in which the tongue 14 and a plurality of teeth 16 are located. In the illustrated exemplary embodiment, a sensor element 18 is arranged on each of the teeth 16 on an inner side of the teeth facing the tongue 14. In some exemplary embodiments, the sensor elements 18 each have a closed outer shell and are adhered to a respective tooth by the outer shell. In other exemplary embodiments, the sensor elements may be attached to a sensor carrier not shown here, wherein the sensor carrier is attached to the user's teeth. In some exemplary embodiments, the sensor carrier may be attached to the user's teeth in a manner similar to braces. Alternatively, the sensor carrier may include a splint made of plastic with a negative shape of the teeth that can be slid over the teeth. Regardless of how the sensor elements are attached to the user's teeth, in some exemplary embodiments, it is preferred to have at least six discrete sensor elements distributed within the oral cavity, with one discrete sensor element disposed on each different tooth.

The input apparatus 10 includes an interface circuit 20 that may include a microcontroller, microprocessor, ASIC, FPGA, or other logic circuit. The interface circuit is held outside of the user's oral cavity in preferred exemplary embodiments. For example, the interface circuit 20 may be held in place by means of a bracket 22 that is attached to one or both of the user's ears in the manner of a headset. In further exemplary embodiments, the interface circuit 20 may be disposed on a necklace or collar that the user may wear around the neck. In further exemplary embodiments, the interface circuit 20 may be arranged on a pair of eyeglass-es or on an eyeglass-like frame, helmet, or similar mount that allows a user to position the interface circuit 20 in the head area. In preferred exemplary embodiments, the interface circuit 20 has an antenna 24 that may extend, for example, in a bracket-like fashion along the jawbone and/or a cheek side of the user, or may be an electronic tattoo applied directly to the user's skin.

In the exemplary embodiment shown here, the interface circuit 20 is connected to an electric drive 26 and a computer 28. The electric drive 26 and the computer 28 are examples of a technical device that the user may operate and/or control using the new input apparatus 10. For example, the drive 26 and the computer 28 may be parts of an assistive robotic system. In general, the input apparatus 10 can be used wherever manual or voice-based data and/or command input for a technical device is not possible, only temporarily possible, or only insufficiently possible, in particular in the field of health care, in military operations such as the adjustment of a telescopic sight in a firing position, or in the field of leisure and sports, such as so-called action sports. In some exemplary embodiments, the interface circuit 20 may be selectively coupled to a plurality of technical devices that are positioned spatially apart from each other, such as in different rooms of a building. The user can then operate and/or control the various technical devices with one and the same input apparatus 10, in each case depending on which of the various technical devices the user is in proximity to at a defined time. Accordingly, in preferred exemplary embodiments, the interface circuit 20 may have a radio interface to the technical device, for example in the form of a WLAN and/or Bluetooth and/or NFC interface.

As schematically indicated in FIG. 1, the interface circuit 20 generates an interrogation signal 30 which is transmitted here via antenna 24 into the oral cavity 12 of the user. The sensor elements 18 each have a transponder—preferably a passive transponder—that is capable of receiving the interrogation signal 30 and generating an individually coded response signal 32, 34 in response thereto. By way of example, a first individual code is shown at reference numeral 32' and a second individual code different therefrom is shown at reference numeral 34'. The response signal 32 with the individual code 32' is generated by a sensor element 18' arranged on tooth 16'. The response signal 34 with the individual code 34' is generated by a sensor element arranged on tooth 16". Based on the different individual codes 32', 34', the interface circuit 20 can identify from which of the sensor elements 18 in the user's oral cavity 12 a respective response signal 32, 34 originates.

In the situation shown in FIG. 1, the tip of the tongue 14 touches the inside of tooth 16' on which the sensor element 18' is arranged. Accordingly, the tongue 14 here covers the sensor element 18', with the result that the response signal 32 is attenuated or even completely suppressed compared to the response signal 34. As a result, the interface circuit 20 receives the response signal 34 from the sensor element 18" at tooth 16" via the antenna 24 much more strongly than the response signal 32 from tooth 16'. The same applies here to further response signals (not shown here) from the further sensor elements 18 in the oral cavity 12 of the user. By analyzing the response signals from all sensor elements 18 in the oral cavity 12, and comparing them to an expectation that may be stored, for example, in an internal memory of the interface circuit 12, the interface circuit 20 may detect that the tongue tip is in contact with tooth 16'. In preferred exemplary embodiments, the interface circuit 20 interprets this as an "actuation" of the sensing element 18' on tooth 16' and it determines a control signal for the technical device in response to this actuation. In some exemplary embodiments, the control signal may correspond to the actuation of a key on a standard computer keyboard, such that the user may generate keystrokes with his or her tongue that are compatible with keystrokes on a standard computer keyboard. In further exemplary embodiments, actuation of the sensing element 18' may, for example, turn the electric actuator 26 on or off.

In preferred exemplary embodiments, the input apparatus 10 includes one or more jaw position sensors 36 that can detect the position of the user's lower jaw relative to the upper jaw and/or a pressure with which the user presses the lower jaw and upper jaw together. The jaw position sensor may also be disposed outside of the oral cavity 12, particularly on the user's skin in the region of the discus articularis. For example, the jaw position sensor may be attached to the temple 22. In preferred exemplary embodiments, the jaw position sensor 36 generates a further individually encoded response signal 38 in response to the interrogation signal 30. The interface circuit 20 may use the jaw position sensor 36 to detect an current jaw position of the user and generate various control signals for the technical device in response thereto. In some exemplary embodiments, the interface circuit 20 may logically combine the jaw position signal 38 in the manner of a toggle button or selection button with actuation of a sensing element 18 by the tongue 14, so that the user may generate different "characters" with the same tongue position or tongue movement by varying his or her jaw position.

In preferred exemplary embodiments, the interface circuit 20 is configured to determine a temporal sequence of tongue positions to thereby detect tongue movement within the oral cavity 12. In some preferred exemplary embodiments, the user may use a controlled tongue movement to cause an interaction with the technical device, such as moving the technical device in a direction of movement corresponding to the direction of movement of the tongue 14.

In preferred exemplary embodiments, the interface circuit 20 analyzes multiple actuations of sensor elements 18 within a defined period of time to detect, in particular, simultaneous or near-simultaneous actuations of sensor elements 18. In some preferred exemplary embodiments, multiple actuations of sensor elements 18 with the tongue 14 can cause a targeted interaction with the technical device, similar to how, for example, simultaneous actuation of multiple keys on the keyboard of a conventional computer can trigger predefined actions. In other exemplary embodiments, the interface circuit 20 may be configured to ignore multiple actuations of sensor elements 18 within the defined time period or compare against a stored expectation for typical uncontrolled tongue movements to filter out unwanted or uncontrolled tongue movements.

Figure 2:
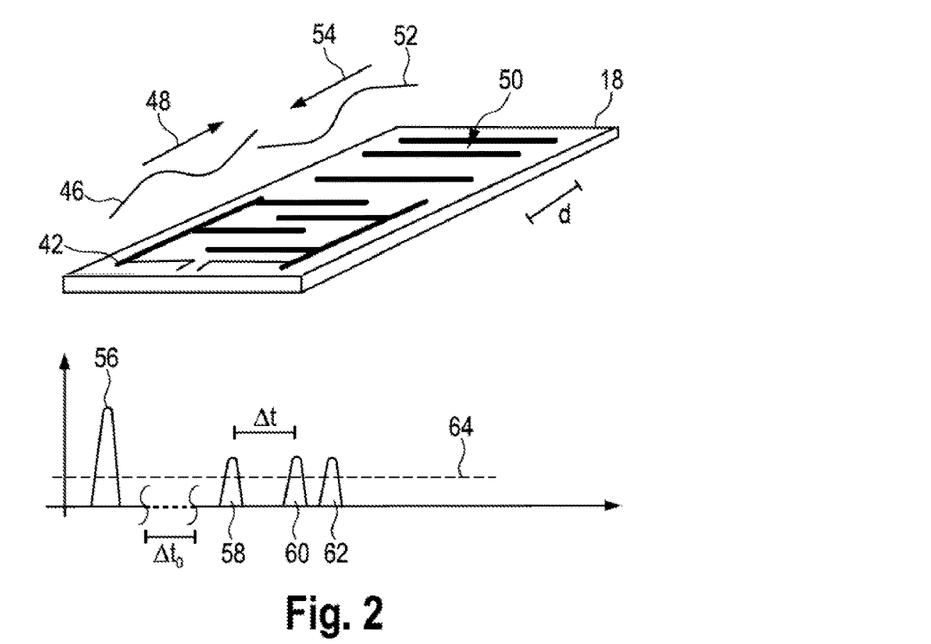
FIG. 2 shows a schematic representation of a SAW tag that can be used as a sensor element in the exemplary embodiment according to FIG. 1.

FIG. 2 shows a preferred exemplary embodiment of a sensor element 18, but here in a schematic view without a biocompatible sheath.

In this case, the sensor element 18 has a body 40 that may be made of, for example, a crystalline semiconductor material, such as lithium niobate LiNbO3. In this case, the body may be very thin and have a thickness of, for example, less than or equal to 0.2 mm. Conductor structures are formed on the body 40, for example as metallic tracks. A first conductor structure 42 forms a wave transducer (interdigital transducer) with a receiving antenna 44 via which the electrical, magnetic and/or electromagnetic interrogation signal 30 can be received. An electrical interrogation signal may be used as part of a capacitive coupling between the sensing elements and the interface circuit. A magnetic interrogation signal may be used in an inductive coupling between the sensor elements and the interface circuit. An electromagnetic interrogation signal 30 corresponds to a radio signal. In principle, all three variants appear possible, although an electromagnetic interrogation signal 30 appears advantageous with respect to the function of the sensor element 18 explained below.

The conductor structure 42 converts the interrogation signal 30 into a surface acoustic wave, indicated at reference numeral 46 in FIG. 2. The surface wave 46 propagates on the surface of the body 40 in the direction of arrow 48. At reference numeral 50, a further conductor structure is shown formed on the surface of the body 40. Here, the further conductor structure 50 includes substantially a plurality of reflectors at which the surface wave 46 is reflected. Consequently, at each reflector of the conductor structure 50, a reflected surface wave 52 is formed which travels in the direction of arrow 54 and reaches the conductor structure 42. There, the returning surface wave 52 is converted back into an electromagnetic wave and radiated via antenna 44.

The conductor structure 42 and the antenna 44 are preferably matched, high impedance, and preferably directly coupled to each other to allow advantageous miniaturization of the sensor element 18. In some exemplary embodiments, the sensor element 18 has a surface area of about 2 mm×2 mm.

In the lower part of FIG. 2, a schematic timing diagram is shown, which shows a pulse at reference numeral 56, symbolizing the interrogation signal 30. The pulse 56 excites an incoming surface wave 46 in the first conductor structure 42. At reference numerals 58, 60, 62, three smaller pulses are shown here, which follow one another in time and occur with a certain time delay $\Delta t_0$ after pulse 56. The pulses 58, 60 are shown here with a temporal spacing $\Delta t$ corresponding to the spatial spacing d between the first two reflectors of the second conductor structure 50 in the direction of travel 48 of the incoming surface wave 46. In other words, the sensor element 18 thus generates a number of temporally staggered response pulses 58, 60, 62 here in response to an interrogation pulse 56, the temporal spacing of the response pulses 58, 60, 62 relative to the interrogation pulse 56 and relative to each other corresponding to the spatial arrangement and distance of the reflectors in the conductor structure 50 relative to the conductor structure 42. The signal strength of the response pulses 58, 60, 62 emitted from the first conductor structure 42 as an electromagnetic wave and then arriving at the antenna 24 of the interface circuit 20 is typically significantly less than the signal strength of the interrogation pulse 56, as simplified in FIG. 2, because the energy of the interrogation pulse 56 is distributed among a plurality of response pulses 58, 60, 62. The time delay $\Delta t_0$ of the response pulses 58, 60, 62 from the interrogation signal 56 is much greater than the time offset from backscatter signals or signal echoes of the interrogation signal 56 due to reflections in the oral cavity because of the propagation speed of the surface acoustic waves 46, 52. The time delay $\Delta t_0$ simplifies the evaluation of the response pulses 60, 62 in the interface circuit 20.

At reference numeral 64, a threshold line is indicated representing a signal threshold stored in the interface circuit 20. Only when a sequence of response pulses 58, 60, 62 exceeds the signal threshold represented by the line 64 does the interface circuit 20 in this exemplary embodiment recognize the corresponding pulse sequence as a response signal from the sensor element 18. The time interval $\Delta t$ of the individual response pulses in the pulse sequence 58, 60, 62 represents an individual coding that uniquely identifies the corresponding sensor element 18. FIG. 2 therefore shows a simplified representation of a so-called SAW tag and an illustration of an advantageous mode of operation. SAW tags have been around since the 1960s and, to a certain extent, they form a geometrically coded transponder that is particularly well suited to the implementation of the new input apparatus because, as passive transponders, SAW tags can be manufactured in a very small size and at low cost. As indicated above, the user can use his tongue to attenuate the signal strength of the electromagnetic wave reaching a SAW tag as an interrogation signal 30, as well as the signal strength of any response pulses 58, 60, 62, thus helping to ensure that the interface circuit 20 does not receive the response signal 32 from the sensing element 18' (see FIG. 1), or at least does not receive it with sufficient signal strength.

Figure 3:
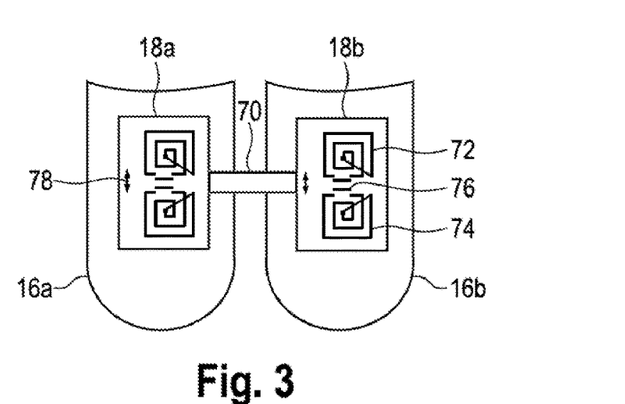
FIG. 3 shows a schematic representation of a further exemplary embodiment with multiple sensor elements.

FIG. 3 shows a further exemplary embodiment based on two sensor elements 18a, 18b, each of which can be arranged on a tooth 16a, 16b of a user. The sensor elements 18a, 18b can be implemented using SAW tags according to FIG. 2 and/or using another transponder technology.

In the exemplary embodiment according to FIG. 3, two adjacent sensor elements 18a, 18b are held on a common sensor carrier 70. As indicated above, the sensor carrier 70 can be made of silicone, plastic or metal and fix one or more sensor elements 18 to the teeth of a user, depending on the application. Suitable sensor carriers 70 are known in principle from the field of dentistry and oral surgery.

A special feature of the exemplary embodiment according to FIG. 3 is that here each of the sensor elements 18a, 18b includes two transmitting/receiving antennas 72, 74, which are arranged spatially adjacent to each other. Each of the two sensor antennas 72, 74 is here "open", i.e., the electrical conductor path of the respective antenna 72, 74 is interrupted. A switch 76 with two contact paths is arranged here between the two antennas 72, 74, The switch 76 can be moved with the tongue in the direction of the double arrow 78 to selectively close one antenna 72 or the other antenna 74. Each of the two antennas 72, 74 of a sensor element 18a, 18b may be coupled to a memory chip in which an individual coding is stored. Therefore, the user may selectively activate the sensor elements 18a, 18b using his or her tongue while selecting which of the respective encodings to send to the interface circuit 20 in response to an interrogation signal 30. With such an exemplary embodiment, it is possible for a sensor element 18a, 18b to selectively transmit different individual encodings and thus transmit different actuations to the interface circuit 20. Furthermore, with an exemplary embodiment according to FIG. 3, the direction of movement of the tongue and, if necessary, an oscillating movement of the tongue can be detected in a simple manner.

Figure 4:
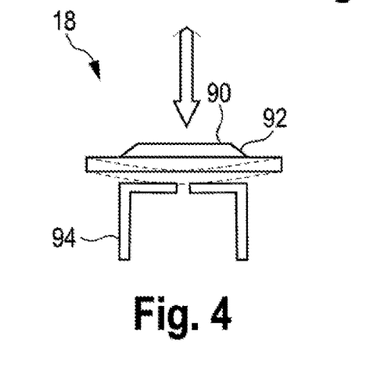
FIG. 4 shows a schematic representation of a sensor element according to a further exemplary embodiment.
Figure 5:
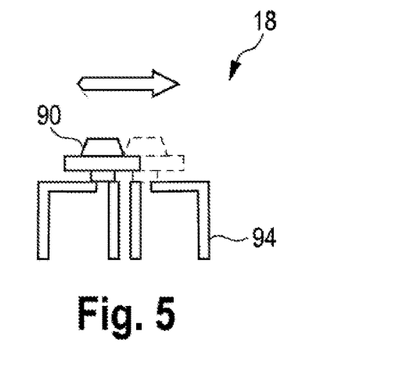
FIG. 5 shows a schematic representation of a sensor element according to yet a further exemplary embodiment.

FIG. 4 shows, in a simplified exemplary embodiment, a sensor element 18 having a contact surface 90 formed here on a protrusion 92. The contact surface 90 can be pressed here by pressure perpendicular to the contact surface 90 onto a conductor track structure 94 in order to close an electrical contact. FIG. 5 shows another exemplary embodiment of a sensor element having a switch, which here must be moved parallel to the contact surface 90 to selectively open or close a dual conductor structure 94. Thus, FIGS. 4 and 5 show possible implementations for a switch 76 according to FIG. 3.

In all preferred exemplary embodiments, the natural movement of the user's tongue 14 over the tooth surfaces facing into the interior of the oral cavity 12 allows for largely fatigue-free operation of the input apparatus 10. The arrangement of a respective single sensor element 18 on a tooth surface enables targeted data and/or control signal generation with a low error rate due to the fine motion skills or fine motion memory of the tongue 14 within the oral cavity 12. An arrangement of the sensor elements on the inner tooth surfaces advantageously contributes to fatigue-free operation. A combined evaluation of the response signals from several sensor elements, possibly in combination with one or more signals representing a jaw position of the user, is particularly advantageous, since in this way a very high number of different input data/commands can be distinguished from each other. Thus, exemplary embodiments of the new input apparatus enable the realization of a keyboard function as known from conventional computer keyboards, but in contrast to a manual actuation here with tongue actuation.

What is claimed is:

1. An input apparatus for at least one of operating or controlling a technical device, the apparatus comprising:
   a plurality of sensor elements configured to be arranged spatially distributed in an oral cavity of a user in order to detect at least one of a respective current tongue position or respective tongue movement of the user, an antenna, an interface circuit coupled to the sensor elements via the antenna, wherein the interface circuit is configured to generate an interrogation signal and transmit the interrogation signal into the oral cavity via the antenna, wherein the sensor elements each include a transponder configured to receive the interrogation signal and to transmit an individually encoded response signal in response to the interrogation signal, with each transponder being configured to generate the individually encoded response signal having an individual code identifying the respective transponder, wherein the transponder is a Surface Acoustic Wave (SAW) tag with an individual coding in the form of a spatial distribution of reflection points, so that the individually coded response signal contains in each case a plurality of reflections whose temporal spacing relative to the interrogation signal and relative to each other represents the individual coding, and wherein the interface circuit is further configured to receive at least one individually encoded response signal from at least one sensor element and to generate a control signal for the at least one of operating or controlling the technical device as a function of the individually encoded response signal.

2. The input apparatus of claim 1, wherein the sensor elements each are arranged on a sensor carrier which is configured to place the sensor elements on the user's teeth.

3. The input apparatus of claim 1, further comprising a holder configured to hold the interface circuit outside the oral cavity.

4. The input apparatus of claim 1, wherein the individually encoded response signals each have a respective signal strength, and wherein the interface circuit is configured to analyze the individually encoded response signals with respect to their respective signal strengths.

5. The input apparatus of claim 4, wherein the interface circuit is configured to compare the respective signal strengths with an expected threshold value.

6. The input apparatus of claim 5, wherein the interface circuit is configured to exclude response signals having a respective signal strength below the expected threshold value from further signal evaluation.

7. The input apparatus of claim 1, wherein the interface circuit is configured to logically interlink a plurality of individually encoded response signals.

8. The input apparatus of claim 1, wherein the sensor elements each include a switch which is configured to selectively activate or deactivate the respective transponder.

9. The input apparatus of claim 8, wherein the sensor elements each have a defined contact surface for the tongue of the user, wherein the switch is configured to be actuated perpendicular to the contact surface.

10. The input apparatus of claim 8, wherein the sensor elements each have a defined contact surface for the tongue of the user, wherein the switch is configured to be actuated parallel to the contact surface.

11. The input apparatus of claim 1, wherein the sensor elements each have at least one of a protrusion or an indentation that provides a tactile marker for the user's tongue.

12. The input apparatus of claim 1, further comprising a jaw position sensor configured to detect a jaw position of the user, wherein the interface circuit is configured to generate the control signal depending on the jaw position sensor.

13. The input apparatus of claim 1, wherein the sensor elements each have a closed biocompatible shell.

14. The input apparatus of claim 1, wherein the transponder is a passive transponder that generates transmission energy required to transmit the individually encoded response signal from the interrogation signal or receives it with the interrogation signal.

15. The input apparatus of claim 1, wherein the transponder is an active transponder having an energy storage in the form of a battery, a rechargeable battery or a super-cap capacitor.

16. A method for at least one of operating or controlling a technical device by a user, comprising the steps:

providing a plurality of sensor elements spatially distributed in an oral cavity of the user, detecting at least one of a respective current tongue position or respective tongue movement of the user using the sensor elements, generating a plurality of control signals depending on the at least one of the respective current tongue position or the respective tongue movement of the user by means of an interface circuit coupled to the sensor elements via an antenna, and transmitting the plurality of control signals from the interface circuit to the technical device, wherein the interface circuit generates an interrogation signal, wherein the sensor elements each include a transponder configured to receive the interrogation signal from the interface circuit via the antenna and to transmit an individually encoded response signal to the interface circuit as a function of the at least one of the respective current tongue position or respective tongue movement of the user, and wherein the transponder is a Surface Acoustic Wave (SAW) tag with an individual coding in the form of a spatial distribution of reflection points, so that the individually coded response signal contains in each case a plurality of reflections whose temporal spacing relative to the interrogation signal and relative to each other represents the individual coding.

* * * * *